US00PP33668P2

(12) United States Plant Patent
Kleinwee

(10) Patent No.: US PP33,668 P2
(45) Date of Patent: Nov. 23, 2021

(54) ***CHRYSANTHEMUM* PLANT NAMED 'CIFZ0081'**

(50) Latin Name: ***Chrysanthemum* x *morifolium***
Varietal Denomination: CIFZ0081

(71) Applicant: SYNGENTA CROP PROTECTION AG, Basel (CH)

(72) Inventor: Theodorus Cornelis Maria Van Kleinwee, Andijk (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 17/243,682

(22) Filed: Apr. 29, 2021

(51) Int. Cl.
*A01H 6/14* (2018.01)
*A01H 5/02* (2018.01)

(52) U.S. Cl.
USPC ..... Plt./298

(58) Field of Classification Search
USPC ..... Plt./298
See application file for complete search history.

*Primary Examiner* — Annette H Para
(74) *Attorney, Agent, or Firm* — Dale Skalla

(57) ABSTRACT

A new garden type *Chrysanthemum* plant named 'CIFZ0081' particularly distinguished by its small to medium size plant with mound plant habit, a small size decorative flower, dark red flower color and a natural season response in mid to late September.

1 Drawing Sheet

Figure 1:
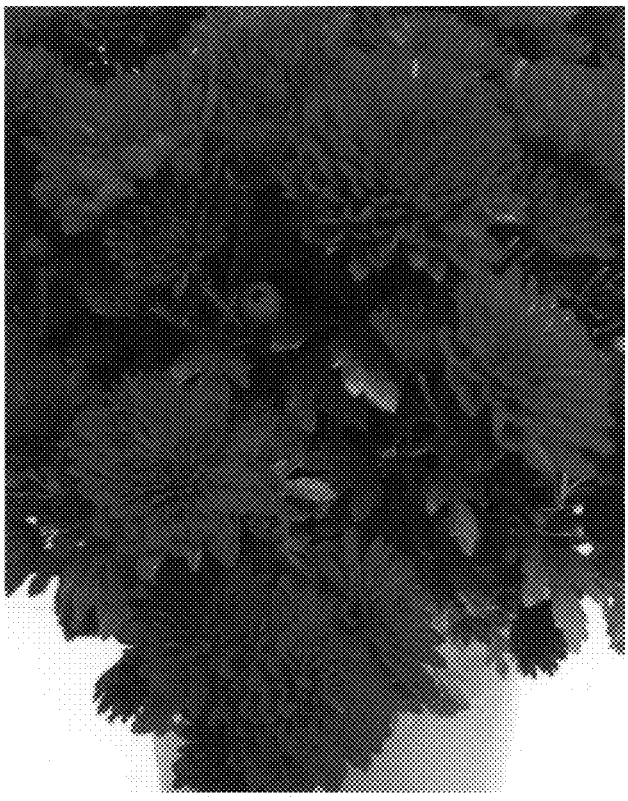

Latin name of the genus and species of the plant claimed: *Chrysanthemum* x *morifolium*.

Varietal denomination: 'CIFZ0081'.

BACKGROUND OF THE NEW PLANT

The present invention comprises a new *Chrysanthemum*, botanically known as *Chrysanthemum* x *morifolium*, and hereinafter referred to by the variety name 'CIFZ0081'.

'CIFZ0081' is a product of a planned breeding program. The new cultivar has small to medium size plant with mound plant habit, a small size decorative flower, dark red flower color and a natural season response in the mid to late September.

'CIFZ0081' originated from a cross made in February 2013 in Enkhuizen, The Netherlands. Seeds were sown in June 2015 in Enkhuizen, The Netherlands and 'CIFZ0081' was selected from the resulting population in the fall of 2015 in Enkhuizen, The Netherlands.

The female parent was an unnamed proprietary seedling '08-M185', dark pink decorative quill.

TABLE 1

Characteristics of the female parent, compared to 'CIFZ0081':

| Trait | 'CIFZ0081' | '08-M185' |
|---|---|---|
| Natural response: | 2.5 weeks slower | 2.5 weeks faster |
| Blackcloth response: | ½ week slower | ½ week faster |
| Flower size: | Smaller | Larger |
| Flower color: | Dark Red | Dark Pink/Lavender |
| Flower type: | Lacks quilled petals | Has quilled petals |
| Plant size: | Larger | Smaller |
| Plant habit: | Similar | Similar |

The male parent was an unnamed proprietary seedling '07-M168', red daisy

TABLE 2

Characteristics of the male parent, compared to 'CIFZ0081':

| Trait | 'CIFZ0081' | '07-M168' |
|---|---|---|
| Natural response: | ½ week slower | ½ week faster |
| Blackcloth response: | Similar | Similar |
| Flower size: | Bit smaller | Bit larger |
| Flower color: | Similar | Similar |
| Flower type: | Decorative | Daisy |
| Plant size: | Larger | Smaller |
| Plant habit: | Similar | Similar |

The first act of asexual reproduction of 'CIFZ0081' was accomplished when vegetative cuttings were propagated from the initial selection in January 2016 in Enkhuizen, The Netherlands.

BRIEF SUMMARY OF INVENTION

Horticultural examination of plants grown from cuttings of the plant initiated in January 2016 and continuing thereafter, has demonstrated that the combination of characteristics as herein disclosed for 'CIFZ0081' are firmly fixed and are retained through successive generations of asexual reproduction.

'CIFZ0081' has not been observed under all possible environmental conditions. The phenotype may vary significantly with variations in environment such as temperature, light intensity and day length.

A Plant Breeder's Right for this cultivar has not yet been applied for. 'CIFZ0081' has not been made publicly available prior to the effective filing date of this application, notwithstanding any disclosure that may have been made less than one year prior to the effective filing date of this application by the inventor or another who obtained 'CIFZ0081' directly from the inventor.

The following traits have been repeatedly observed and are determined to be basic characteristics of the new variety.

The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0081' with colors being as true as possible with an illustration of this type.

Figure 2:
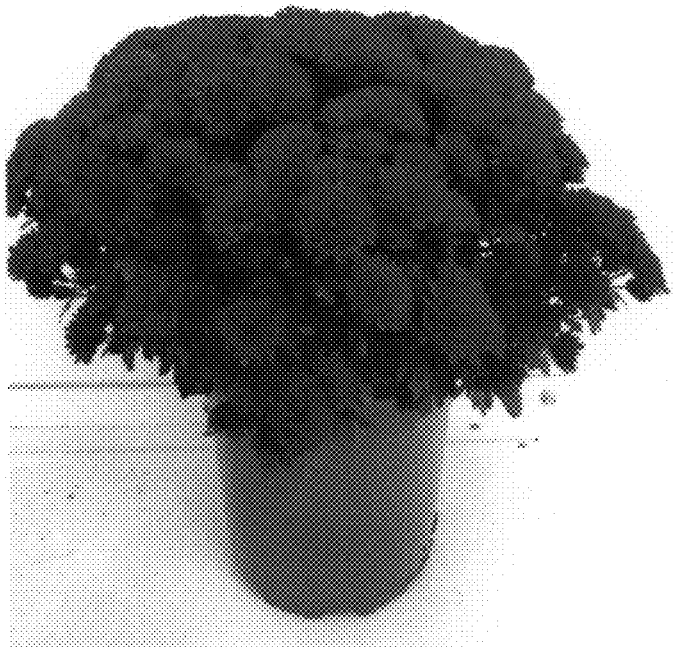

The photographic drawing shows in FIG. 1 a close view of flower of the new variety and in FIG. 2 a flowering plant from an outdoor trial.

The aforementioned photographs: FIG. 1, as well as FIG. 2 were taken in September 2020 both showing a plant from the same blackcloth outdoor trial in Enkhuizen, The Netherlands.

These plants were about 12 weeks of age. One rooted cutting per pot had been planted in a 19 cm pot, not pinched in week 24, and black clothed from week 29. Plants started flowering the end of August.

DETAILED BOTANICAL DESCRIPTION

The measurements were taken in Enkhuizen, the Netherlands in September 2020 on the plants from the aforementioned trial.

Color references are made to The Royal Horticultural Society Colour Chart (R.H.S.) 2001

TABLE 3

DIFFERENCES BETWEEN THE NEW VARIETY 'CIFZ0081' AND TWO MOST SIMILAR VARIETIES:

| Trait | 'CIFZ0081' | 'Yobrandi' (U.S. Plant Pat. No. 16,134) |
|---|---|---|
| Natural response: | Similar | Similar |
| Blackcloth response: | Similar | Similar |
| Flower size: | ¼ inch smaller | ¼ inch larger |
| Flower color: | Similar | Similar |
| Flower type: | Similar | Similar |
| Plant size: | Taller | Shorter |
| Plant habit: | Rounder | Shorter/Wider |
| Flower longevity: | 15% Shorter | 15% Longer |

TABLE 4

| Trait | 'CIFZ0081' | 'Zanmuryder' (U.S. Plant Pat. No. 24,646) |
|---|---|---|
| Natural response-North: | Similar | Similar |
| Natural response-South: | 1 week faster | 1 week slower |
| Blackcloth response: | 1.5 weeks faster | 1.5 weeks slower |
| Flower size: | Similar | Similar |
| Flower color: | Similar | Similar |
| Flower type: | Similar | Similar |
| Plant size: | Bit smaller | Bit larger |
| Plant habit: | Similar | Similar |
| Flower longevity: | Shorter | Longer |
| Foliage color: | Greener | Yellower |

Plant:

*Form, growth and habit.*—Herbaceous garden-type, stems Upright and outwardly spreading, freely branching, strong and moderately vigorous growth habit.

*Plant height (above soil).*—17 cm.

*Plant height (inflorescence included).*—22 cm.

*Plant width.*—37 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B.

Foliage:

*Arrangement.*—Alternate.

*Immature leaf, color upper surface.*—RHS 147A.

*Immature leaf, color lower surface.*—RHS 137C.

*Mature leaf, color, upper surface.*—RHS 147A.

*Mature leaf, color lower surface.*—RHS 137B.

*Length.*—6.1 cm.

*Width.*—3.6 cm.

*Shape.*—Ovate, with distinct lobes.

*Base shape.*—Attenuate.

*Apex shape.*—Mucronate.

*Margin.*—5-lobed (palmate), edge dentate.

*Number of margin indentations.*—Medium.

*Depth of margin indentations.*—Deep.

*Leaf length terminal lobe relative to total leaf length.*—Long.

*Leaf depth lower lateral sinus.*—Shallow to medium.

*Texture, upper surface.*—Bifid hairs.

*Texture, lower surface.*—Bifid hairs.

*Color of veins, upper surface.*—RHS 147C.

*Color of veins, lower surface.*—RHS 147C.

*Pattern of veining.*—Palmate.

*Petiole color.*—RHS 147C.

*Petiole length.*—1.6-2.0 cm.

*Diameter.*—0.3 cm.

*Texture.*—Bifid hairs.

*Presence of stipules.*—No.

Stem:

*Quantity of main branches per plant.*—6-8.

*Color of stem.*—RHS 147A with some anthocyanin spots RHS N92A.

*Length of stem.*—8.0-9.0 cm.

*Diameter.*—0.6 cm.

*Length of internodes.*—1.3-3.5 cm.

*Texture.*—Bifid hairs.

*Color of peduncle.*—RHS 146B.

*Length of peduncle.*—4.0 cm.

*Peduncle diameter.*—0.3 cm.

*Texture.*—Bifid hairs.

Inflorescence:

*Type.*—Compositae, solitary, decorative-type inflorescences borne terminally above foliage, ligulate ray florets arranged acropetally on a capitulum giving a double flower.

*Quantity of short days to flowering (response time).*—Approximately 7 weeks.

*Natural season flowering.*—Mid to Late September.

*Quantity of inflorescences per plant.*—130-150 with many small buds developing.

*Lastingness of individual blooms on the plant.*—About five weeks from first color.

*Fragrance.*—Slightly spicy.

Bud (when showing color):

*Color.*—RHS 185A.

*Length.*—1.0 cm.

*Width.*—0.9 cm.

*Shape.*—Oblate.

Immature inflorescence (at moment of opening):
*Diameter.*—2.0 cm.
*Color of ray florets, upper surface.*—RHS 187C.
*Color of ray florets, lower surface.*—RHS 46A.
Mature inflorescence:
*Diameter.*—3.8 cm.
*Depth.*—1 cm.
*Total diameter of disc.*—No disc present.
*Receptacle color.*—RHS 146B, stripes 146A.
*Receptacle height.*—0.4 cm.
*Receptacle diameter.*—1.3 cm.
*Length of corolla tube.*—Short.
Ray florets:
*Average quantity of florets.*—140-150 in several whorls.
*Color of florets, upper surface.*—RHS 187C.
*Color lower surface.*—RHS 46A, some yellow stripes RHS 8C on petals of inner whorls.
*Length.*—1.6 cm.
*Width/diameter.*—0.4 cm.
*Shape.*—Elliptical.
*Apex shape.*—Mostly obtuse, occasionally slightly dentate.
*Base shape.*—Tube.
*Margin.*—Entire — Small incisions may be present at tip.
*Margin.*—Type of rolling — Moderately involute.
*Texture, upper surface.*—Papillate.
*Lower surface.*—Papillate.
*Ribs present.*—No.
*Number of keels.*—0.
*Profile at widest point.*—Weakly convex.
*Longitudional axis shape.*—Reflexing.
Disc florets:
*Number of disc florets.*—No development of disc florets.
Inflorescence (at moment of senescence):
*Color of ray florets, upper surface.*—RHS 187B.
*Color of ray florets, lower surface.*—RHS 53A.
Phyllaries:
*Quantity.*—20-25.
*Color, upper surface.*—RHS 146B.
*Color, lower surface.*—RHS 146D.
*Length.*—0.6 cm.
*Width.*—0.1-0.2 cm.
*Shape.*—Lanceolate.
*Apex shape.*—Acute.
*Base.*—Fused.
*Margins.*—Entire.
*Texture, upper surface.*—Glabrous.
*Texture, lower surface.*—Canescent.
Reproductive organs:
*Pistil.*—One.
*Length.*—0.4 cm.
*Style color.*—RHS 150C.
*Style length.*—0.3 cm.
*Stigma color.*—RHS 8D.
*Stigma shape.*—Bi-parted.
*Ovary color.*—RHS 145B.
*Ovary length.*—0.2 cm.
*Ovary width.*—0.1 cm.
Androecium: No disc florets developed and no androecium developed.
*Disease/pest resistance.*—Has not been determined to date.
*Hardiness.*—Has not been determined to date.

What is claimed is:

1. A new and distinct variety of *Chrysanthemum* plant named 'CIFZ0081' substantially as illustrated and described herein.

* * * * *